United States Patent
Koch

(10) Patent No.: US 6,616,599 B2
(45) Date of Patent: Sep. 9, 2003

(54) PROCESS AND SYSTEM FOR REGULATING THE AIR TEMPERATURE IN AN INCUBATOR

(75) Inventor: Jochim Koch, Ratzeburg (DE)

(73) Assignee: Dräger Medical AG & Co. KGAA (DE)

( * ) Notice: Subject to any disclaimer, the term of this patent is extended or adjusted under 35 U.S.C. 154(b) by 0 days.

(21) Appl. No.: 10/104,773

(22) Filed: Mar. 21, 2002

(65) Prior Publication Data

US 2002/0188168 A1 Dec. 12, 2002

(30) Foreign Application Priority Data

Jun. 7, 2001 (DE) .......................................... 101 27 793

(51) Int. Cl.⁷ .............................................. A61G 11/00
(52) U.S. Cl. ........................................................ 600/22
(58) Field of Search ...................... 600/21, 22; 219/385, 219/203, 526, 527, 543, 405, 411; 5/93.1

(56) References Cited

U.S. PATENT DOCUMENTS

| | | | |
|---|---|---|---|
| 3,920,000 A | * 11/1975 | Atherton et al. ............... | 600/22 |
| 4,161,172 A | * 7/1979 | Pickering ...................... | 600/22 |
| 5,352,869 A | * 10/1994 | Barsky ......................... | 219/543 |
| 5,498,229 A | * 3/1996 | Barsky et al. ................. | 600/22 |
| 5,649,896 A | * 7/1997 | Barsky ......................... | 600/22 |
| 5,817,003 A | 10/1998 | Moll et al. | |
| 6,210,320 B1 | * 4/2001 | Rogone et al. ................ | 600/22 |
| 6,464,627 B1 | * 10/2002 | Falk ............................. | 600/22 |

* cited by examiner

*Primary Examiner*—Samuel G. Gilbert
(74) *Attorney, Agent, or Firm*—McGlew and Tuttle, P.C.

(57) ABSTRACT

A process and system is provided for regulating the air temperature in an incubator (3), which accommodates a patient, especially a premature or newborn infant, and which is part of a so-called hybrid device. When the function of the hybrid device is changed over between the two device types of "closed incubator" and "open care unit," the problem arises that the air temperature set point cannot be maintained and the patient cools down as a consequence. The process uses a heat radiation source (1), which is located outside the incubator (3), which can be closed with a hood (2) that is transparent to the radiated heat. The corresponding value measured by an air temperature sensor (5), which is used as an actual air temperature value, is evaluated by an evaluating and control unit (4) along with a value measured by a body temperature sensor (7). When the actual values that continue to be measured by the air temperature sensor (5) exceed a preset set point, the radiation dose of the heat radiation source (1) is reduced, and increased in the contrary case, until the preset set point and the actual value of the air temperature sensor (5) agree.

20 Claims, 2 Drawing Sheets

PROCESS AND SYSTEM FOR REGULATING THE AIR TEMPERATURE IN AN INCUBATOR

FIELD OF THE INVENTION

The present invention pertains to a process for regulating the air temperature in an incubator accommodating a patient and more particularly to a hybrid device combining essentially an incubator and a heat radiation source.

BACKGROUND OF THE INVENTION

An incubator that is part of a so-called hybrid comprises essentially an incubator and a heat radiation source and as a result combines the advantages of two types of devices. A comfortable climate can be reliably established for a patient with a closed incubator, and a heat radiation source above an open care unit facilitates the access to the patient for care and supply procedures. The function of hybrids can be changed from one type of device to the other or vice versa, i.e., from a closed incubator to an open care unit, with little effort. Closed incubators produce the necessary climate usually by means of convection heating and a moisture evaporator, and open care units are heated by means of heat radiation sources. The problem arising in connection with changing the function of the hybrid from one type of device to the other is that the air temperature in the hybrid cannot be reliably maintained for the patient. When the incubator is opened the heat radiation source is used instead of the convection heating, or vice versa. When the incubator is closed, the heat radiation source is switched off and the convection heating is switched on instead. The temperature in the incubator drops greatly during a certain period in both cases causing the cooling of the patient in the meantime.

A hybrid and a process for maintaining the body temperature of a patient during a changeover from one type of device to the other are described in U.S. Pat. No. 5,817,003. This goal is accomplished only insufficiently by the design of the hybrid and with the process used therein for the enmeshed regulation of the output of the convection heater and the heat radiation source. The changeover in a hybrid from the device type of an open care unit to the device type of a closed incubator therefore leads to irregular fluctuations in the patient's body temperature. At equal air temperature, a heat radiation source causes a higher temperature on the skin surface of a patient than a convection heater. If, e.g., the temperature on the skin surface of the patient is now used to determine his body temperature, different conversion methods must be used in the two cases. If this difference is not taken into account, the body temperature will be inevitably incorrect. At the time of the changeover from the heat radiation source of the open care unit to the convection heating of the closed incubator, the heat radiation source is lowered together with the incubator hood to close the incubator. However, the heat radiation source must have cooled sufficiently before it comes close to the patient in this manner in order to prevent burning the patient due to the unintended contact. Since the infrared radiation sources used for this purpose in practice frequently have surface temperatures of a few hundred degrees, there also is a fire hazard at increased oxygen concentration or in the case of the use of disinfectants containing alcohol. The transition time between the two device types is therefore always a few minutes in order to ensure that the infrared radiation source will have cooled sufficiently at the time of the transition from the open care unit to the closed incubator before it reaches the vicinity of the patient and conversely, the infrared radiation source already has a sufficient distance from the patient before it heats up at the time of the transition from the closed incubator to the open care unit. The air temperature in the incubator of the hybrid can be maintained only insufficiently during this transition time, so that a patient located herein will cool off. Furthermore, it may be necessary to open the hood of an incubator immediately. Preheating by switching on the heat radiation source in advance is no longer possible. The convection heating of the opened incubator is already switched off and the heat radiation source is not heated up, so that the patient will cool off.

To avoid the risk of burn for the patient or a fire hazard, the infrared radiation source in a hybrid can be covered during the transition time between the two types of device with an automatically opening and closing flap. The transition times during the changeover between the two types of device, during which the body temperature of the patient decreases, are thus shortened. However, this requires complicated technical measures and may lead to an alleviation, but not to the elimination of the problem of the insufficient regulation of the air temperature for maintaining the patient's body temperature in the hybrid.

SUMMARY AND OBJECTS OF THE INVENTION

The object of the present invention is to provide a process for regulating the air temperature in an incubator for a patient, which guarantees that the body temperature is also maintained during the changeover between the different types of device.

According to the invention a process is provided for regulating the air temperature in an incubator which accommodates a patient, can be closed, is transparent to heat radiation and is exposed to the radiation of a heat radiation source. An air temperature sensor is provided in the incubator. An evaluating and control unit evaluates the signals received from the air temperature sensor and controls the radiation dose delivered by the heat radiation source. The air temperature sensor receives an actual value $T_I$ for the air temperature, which is sent to the evaluating and control unit. The evaluating and control unit compares the actual value $T_I$ with an internally preset set point $T_S$, forming the difference $T_S-T_I$ from the two values and generating a manipulated variable from the difference for the heat radiation source. If $T_S-T_I>0$, the radiation dose of the heat radiation source is increased, and if $T_S-T_I<0$, the radiation dose of the heat radiation source is reduced until $T_S-T_I=0$ is reached.

The process for regulating the air temperature in an incubator accommodating a patient uses a heat radiation source, preferably an infrared radiation source, which sends heat radiation to a patient in the incubator. The temperature in the interior of the incubator is measured by the air temperature sensor. This actual value $T_I$ for the air temperature is sent to an evaluating and control unit and is compared with an internally preset set point $T_S$ for the air temperature in the interior of the incubator. The difference $T_S-T_I$ is formed from the actual value $T_I$ and the set point $T_S$ for the air temperature. A manipulated variable for the heat radiation source is generated from the difference $T_S-T_I$ in such a way that if $T_S-T_I>0$, i.e., the actual value is lower than the set point of the air temperature, the radiation dose of the heat radiation source is increased and if $T_S-T_I<0$, i.e., the actual value is greater than the set point of the air temperature, the radiation dose of the heat radiation source is reduced until $T_S-T_I=0$, i.e., the actual value and the set point agree. Incorrect regulation of the patient's body temperature, which is due to the fact that an air temperature is preset without taking into account whether it was brought about by convection heating or a heat radiation source, is avoided by using only one heat radiation source for the temperature regulation according to the process according to the present invention.

In a preferred embodiment of the present invention, the heat radiation source is installed stationarily in relation to the incubator of the hybrid device for the patient, i.e., there is a constant distance between the heat radiation source and the incubator.

The heat radiation source emits uninterrupted radiation. Undesired long heat-up times, which are due to the fact that when the heat radiation source is switched on, it must first heat up completely before the intended output is reached, are thus avoided. The incubator of the hybrid device for accommodating the patient can be closed with a hood that is transparent to the radiation of the heat radiation source. The climate in the incubator can thus be maintained better in regard to the temperature, the relative humidity and the oxygen content. The air temperature sensor in the interior of the incubator has a screen that is non transparent to the radiation of the heat radiation source. It is ensured as a result that the results of the measurement are not distorted by radiation reaching the air temperature sensor. In the process for regulating the air temperature in the incubator, which accommodates a patient, an actual value for the air temperature, which was measured by the air temperature sensor, is compared with an internally preset set point. In a preferred embodiment of the process, the patient's body temperature value is first determined with at least one body temperature sensor, e.g., a skin temperature sensor, and is sent to the evaluating and control unit. Actual values for the air temperature in the incubator are received during this time by the air temperature sensor and these are likewise sent to the evaluating and control unit. The evaluating and control unit then presets a set point for the air temperature in such a manner that this corresponds to a desired body temperature value of the patient. Maintenance of a desired body temperature value of the patient is achieved as a result by the regulation of the air temperature. Desired body temperature values are here especially the so-called core temperature, which is determined in the known manner from a skin temperature measurement at the head or on the chest of the patient and the linking by calculation with the ambient temperature of the patient, or the so-called peripheral temperature, which is determined from a skin temperature measurement on the extremities and the linking by calculation with the patient's ambient temperature.

The relative humidity and the oxygen content in the air in the incubator are also regulated, in particular, besides the regulation of the air temperature. If enrichment with fresh air is performed such that a continuous fresh air supply with bacteria filtering generates a slight overpressure on the order of magnitude ranging from a fraction of one Pascal to a few Pascals in the closed incubator, it is thus ensured that no air will enter from the outside through smaller openings or leaks.

A mattress for the patient, which is equipped with a mattress heater in a preferred embodiment, which is controlled especially by the evaluating and control unit, is located in the incubator. The mattress heater has a temperature control which is operated separately from the air temperature regulation in the incubator.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
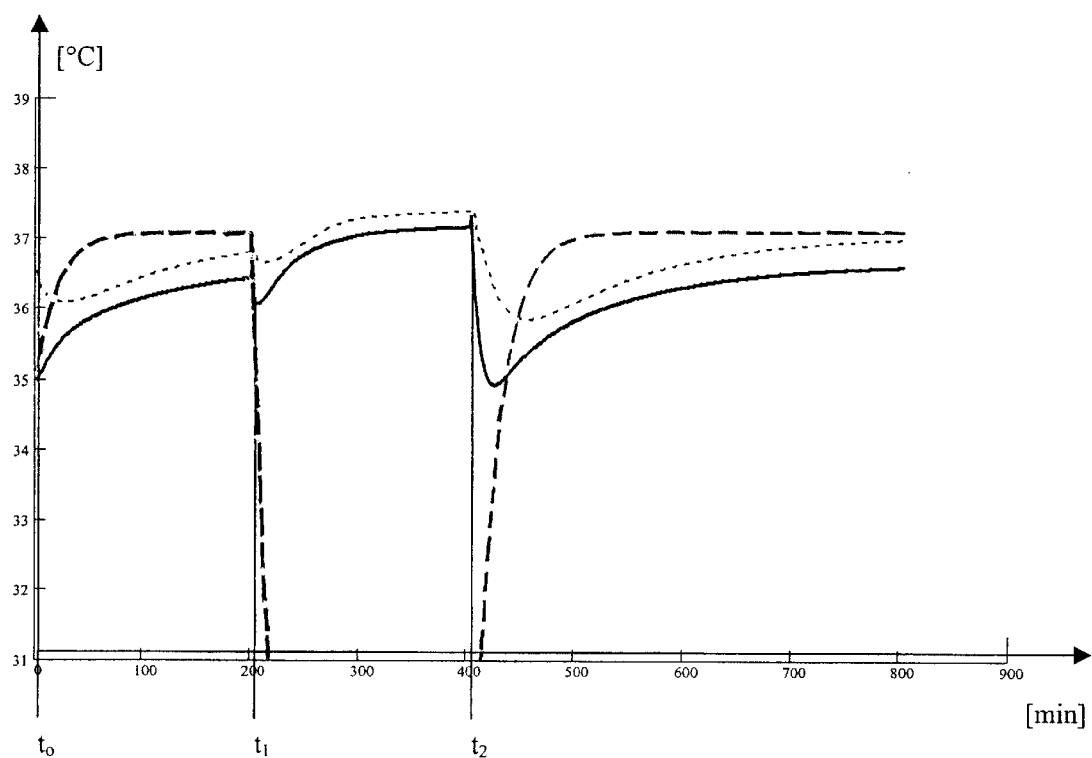
FIG. 1 is a diagram showing the changes in the core temperature and the skin temperature over time in the case of a premature infant as well as in the air temperature in the incubator for the premature infant in a hybrid according to the prior art.

Referring to the drawings in particular, FIG. 1 shows the changes in the core temperature over time as a dotted line, and the changes in the skin temperature of a premature infant over time as a solid line. The premature infant weighs 500 g, was born in week 26 of pregnancy and is 4 days old. The air temperature in the incubator for the premature infant in a hybrid according to the prior art is represented as a broken line. The temperatures are always plotted in degrees Celsius (° C.) over the time in minutes (min.).

The premature infant is placed into the incubator at time $t_0=0$, the incubator is closed, and the convection heating is switched on. The air temperature in the incubator rapidly rises from 35° C. to 37° C., the skin temperature of the premature infant rises with a slight time delay, and only from 35° C. to 36° C. The core temperature of the premature infant decreases during the same period from 36.5° C. first to 36° C., due to the initially somewhat cooler air temperature in the incubator, but it gradually rises again thereafter to 36.5° C. All temperatures have stabilized by the time $t_1=200$: The air temperature in the incubator is 37° C., the skin temperature of the premature infant is 36° C., and the core temperature is 36.5° C. The convection heating is switched off at time $t_1=200$, the incubator is opened, and a heat radiation source directed toward the incubator is switched on. As a consequence, the air temperature in the incubator drops abruptly to 31° C., the skin temperature and the core temperature of the premature infant decrease only slightly during a short period of time, after which the core temperature rises approximately to a value of 37° C., the skin temperature likewise rises to nearly 37° C. and reaches a higher value than in the case of the closed incubator with the convection heating switched on. All temperatures have again stabilized at the time $t_2=400$: The air temperature in the opened incubator is 31° C., the skin temperature of the premature infant is approximately 37° C., and the core temperature is somewhat higher than 37° C. The convection heating is again switched on at the time $t_2=400$, the incubator is closed, and the heat radiation source directed toward the incubator is switched off. The consequence of this is that the air temperature in the incubator rises again very rapidly to 37° C., whereas the core temperature decreases abruptly to 35.5° C. and the skin temperature to 34.5° C. All temperatures are again stabilized after a certain time: The air temperature in the closed incubator and the core temperature of the premature infant are stabilized at approximately 37° C., and the skin temperature of the premature infant at 36° C.

Figure 2:
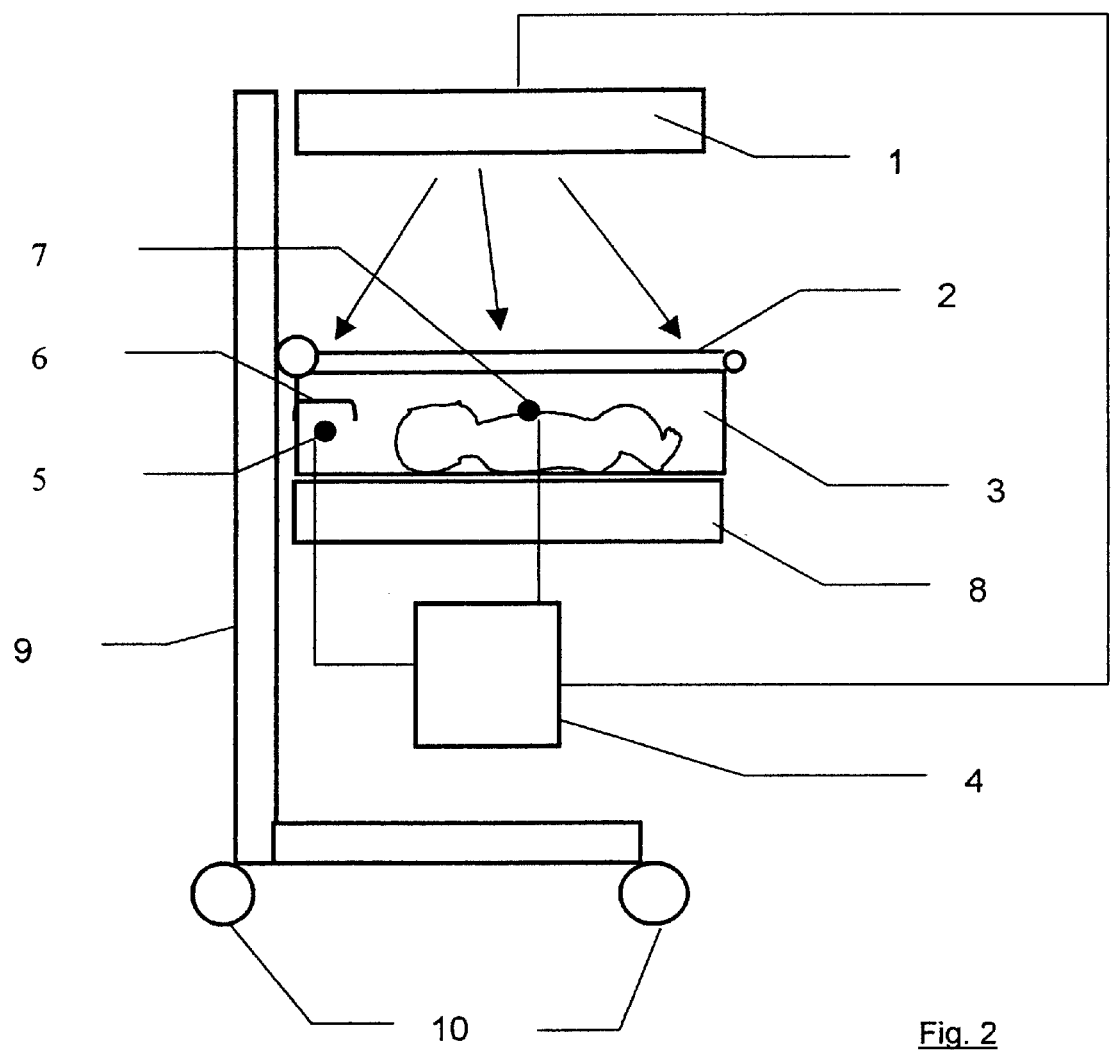
FIG. 2 is a schematic view of a hybrid that can be operated according to the process according to the present invention.

In summary, it can be stated that unacceptable changes occur in both the core temperature and the skin temperature of the premature infant at the time of the changeover from the closed hybrid with convection heating to the open hybrid with heat radiation source and vice versa. The process according to the present invention, which can be carried out with the hybrid shown in FIG. 2, is a solution to this problem. The hybrid comprises an incubator 3 for accommodating a patient, for whom a mattress 8 located on the bottom of the incubator 3 is provided. The incubator 3 can be closed with a cover that is transparent to heat radiation, especially a hood 2 or a film. A bracket 9 for the hybrid device has rollers 10, which make possible the mobile use of the hybrid device, A heat radiation source 1 sends heat radiation, represented by three downwardly pointing arrows, through the closed hood 2 onto the patient lying on the mattress 8 in the incubator 3. A skin temperature sensor 7 measures the skin temperature of the patient. An air temperature sensor 5 measures the air temperature in the incubator 3. The air temperature sensor 5 is protected from the rays of the heat radiation source 1 by a screen 6 that is not transparent to the radiation. The signals received from the air temperature sensor 5 and the skin temperature sensor 7 are sent to an evaluating and control unit 4. For a preset skin temperature value, the evaluating and control unit 4 first determines the air temperature value that corresponds to the preset skin temperature value of the patient. This air temperature value is the internally preset set point $T_S$ of the process according to the present invention for regulating the air temperature. An air temperature value measured by the air temperature sensor 5 is the actual value $T_I$. The evaluating and control unit 4 forms the difference $T_S-T_I$ and generates a manipulated variable therefrom for the heat radiation source 1 in such a manner that if $T_S-T_I>0$, the radiation dose of the heat radiation source 1 is increased and if $T_S-T_I<0$, the radiation dose of the heat radiation source 1 is reduced until $T_S-T_I=0$ is reached.

While specific embodiments of the invention have been shown and described in detail to illustrate the application of the principles of the invention, it will be understood that the invention may be embodied otherwise without departing from such principles.

What is claimed is:

1. A process for regulating air temperature in an incubator, which accommodates a patient, can be closed, is transparent to heat radiation and is exposed to radiation of a heat radiation source, with an air temperature sensor in the incubator and with an evaluating and control unit, which evaluates signals received from the air temperature sensor and controls a radiation dose delivered by the heat radiation source, the process comprising the steps of:
    sensing the air temperature with the air temperature sensor to provide an actual air temperature value $T_I$ and sending the actual air temperature value to the evaluating and control unit;
    comparing with the evaluating and control unit the actual value $T_I$ with an internally preset set point $T_S$ for the air temperature, forming a difference $T_S-T_I$ from the two values and generating a manipulated variable from the difference $T_S-T_I$ for the heat radiation source;
    increasing the radiation dose of the heat radiation source if $T_S-T_I>0$; and
    decreasing the radiation dose of the heat radiation source if $T_S-T_I<0$, the radiation dose of the heat radiation source is reduced until $T_S-T_I=0$ is reached.

2. A process in accordance with claim 1, further comprising: arranging the heat radiation source at a constant distance outside the incubator and independent of whether the incubator is opened or closed.

3. A process in accordance with claim 1, wherein the heat radiation source emits uninterrupted radiation.

4. A process in accordance with claim 1, further comprising: providing the the incubator with a hood that is transparent to the radiation of the heat radiation source to open and close the incubator.

5. A process in accordance with claim 1, further comprising: providing the air temperature sensor with a screen that is nontransparent to the radiation of the heat radiation source.

6. A process in accordance with claim 1, further comprising: at least one bocy temperature sensor first determining a patient's body temperature value and sending it to the evaluating and control unit, which determines therefrom the set point $T_S$ for the air temperature in such a manner that this set point corresponds to a desired body temperature value of the patient.

7. A process in accordance with claim 1, wherein a means for regulated air humidification is provided in the incubator.

8. A process in accordance with claim 1, wherein a means for regulated enrichment with oxygen is provided in the incubator.

9. A process in accordance with claim 1, further comprising: performing continuous enrichment with fresh air in such an amount that a slight over pressure is generated ranging from fractions of one Pascal to a few Pascals in the incubator.

10. A process in accordance claim 1, wherein a heating mattress is provided in the incubator and is controlled by the evaluating and control unit.

11. A system for regulating the air temperature in an incubator, the system comprising:
    an incubator which accommodates a patient, the incubator being openable and closable and having at least a portion transparent to heat radiation;
    a heat radiation source, the portion of the incubator transparent to heat radiation being exposed to radiation of the heat radiation source;
    an air temperature sensor in the incubator; and
    an evaluating and control unit for evaluating air temperature signals representing an actual air temperature value $T_I$ received from the air temperature sensor, comparing the actual value $T_I$ with an internally preset set point value $T_S$, forming a difference $T_S-T_I$ from the two values and generating a manipulated variable from the difference $T_S-T_I$ for controlling the heat radiation source and controlling a radiation dose delivered by the heat radiation source by increasing the radiation dose of the heat radiation source if $T_S-T_I>0$ and decreasing the radiation dose of the heat radiation source if $T_S-T_I<0$, the radiation dose of the heat radiation source is reduced until $T_S-T_I=0$ is reached.

12. A system in accordance with claim 11, wherein the heat radiation source is positioned at a constant distance outside the incubator.

13. A system in accordance with claim 11, wherein the air temperature sensor has a screen that is nontransparent to the radiation of the heat radiation source.

14. A system in accordance with claim 11, further comprising a body temperature sensor for first determining a patient's body temperature value and sending the body temperature value to the evaluating and control unit, the evaluating and control unit determining a set point $T_S$ for the air temperature in such a manner that the set point corresponds to a desired body temperature value of the patient.

15. A system in accordance with claim 11, further comprising means for regulated enrichment of the interior of the incubator with oxygen.

16. A system in accordance with claim 11, wherein continuous enrichment with fresh air is performed to generate a slight overpressure ranging from a fraction of one Pascal to a few Pascals in the incubator.

17. A system in accordance claim 11, further comprising a heated mattress in the incubator controlled by the evaluating and control unit.

18. A process for regulating air temperature in an incubator, the process comprising the steps of:

providing a cover movable on the incubator to open and close the incubator, said cover being transparent to heat radiation;

providing a heat radiation source spaced from the incubator and said cover, said heat radiation source directing heat into the incubator;

measuring actual air temperature in the incubator;

providing a desired air temperature as a set point;

comparing said actual air temperature and said desired air temperature;

determining if said actual air temperature is higher than said desired air temperature if said actual air temperature is lower than said desired air temperature;

decreasing radiation from said heat radiation source to the incubator if said actual air temperature is higher than said desired air temperature, said decreasing being performed independently of the incubator being opened or closed;

increasing radiation from said heat radiation source to the incubator if said actual air temperature is lower than said desired air temperature, said increasing being performed independently of the incubator being opened or closed.

19. A process in accordance with claim 18, wherein:

said decreasing and said increasing are performed exclusively on said determining if said actual air temperature is higher or lower than said desired air temperature.

20. A process in accordance with claim 18, wherein:

said providing of said desired air temperature includes comparing a body temperature of a patient in the incubator with a corresponding air temperature in the incubator.

* * * * *